(12) United States Patent
Aijima

(10) Patent No.: US 6,431,002 B1
(45) Date of Patent: Aug. 13, 2002

(54) AUTOMATIC ULTRASONIC FLAW DETECTOR

(75) Inventor: Masatoshi Aijima, Tokyo (JP)

(73) Assignee: Jamco Corporation, Tokyo (JP)

( * ) Notice: Subject to any disclaimer, the term of this patent is extended or adjusted under 35 U.S.C. 154(b) by 44 days.

(21) Appl. No.: 09/698,275

(22) Filed: Oct. 30, 2000

(30) Foreign Application Priority Data

Nov. 1, 1999  (JP) ............................................ 11-310609

(51) Int. Cl.$^7$ .......................... G01N 29/06; G01N 29/10
(52) U.S. Cl. ................................ 73/620; 73/644; 73/627
(58) Field of Search .......................... 73/620, 622, 624, 73/625, 627, 628, 629, 644

(56) References Cited

U.S. PATENT DOCUMENTS

| | | | | |
|---|---|---|---|---|
| 3,400,363 A | * | 9/1968 | Silverman | 342/179 |
| 3,828,609 A | * | 8/1974 | Furon et al. | 73/622 |
| 4,489,611 A | * | 12/1984 | Zimmermann et al. | 73/625 |
| 4,644,510 A | * | 2/1987 | Fujii | 367/87 |
| 4,677,842 A | * | 7/1987 | Piche | 73/32 A |
| 4,848,159 A | * | 7/1989 | Kennedy et al. | 73/588 |
| 5,629,865 A | * | 5/1997 | Roth | 702/56 |
| 6,089,095 A | * | 7/2000 | Yang et al. | 73/600 |

* cited by examiner

*Primary Examiner*—Hezron Williams
*Assistant Examiner*—Rose M. Miller
(74) *Attorney, Agent, or Firm*—Armstrong, Westerman & Hattori, LLP

(57) ABSTRACT

A tank 10 has an opening through which enters a molded material $P_1$, which is the object of inspection, and water $W_1$ is filled within the tank 10. One side wall of said tank 10 is equipped with the plurality of ultrasonic search units 40. On the other side wall of said tank 10 is mounted a reflector plate 100 opposing to said ultrasonic search units 40. The reflection surface 100a of said reflector plate 100 is positioned away from the surface of an object portion $P_{10}$ by a predetermined distance $D_1$. The ultrasonic waves generated from the search units are reflected, and the reflected waves are transduced into electric signals, and the signals are compared with the signals received from the solid portion, so as to detect flaw.

5 Claims, 9 Drawing Sheets

AUTOMATIC ULTRASONIC FLAW DETECTOR

FIELD OF THE INVENTION

The present invention relates to an automatic ultrasonic flaw detector for detecting the inner flaw or defect of a molded material made of plastic, composite material or metal.

DESCRIPTION OF THE RELATED ART

For example, a molded material formed of composite material has an L-shaped, T-shaped or H-shaped cross section. The molded material is formed along the longitudinal direction.

In order to inspect any flaw or defect existing within the molded material, an ultrasonic flaw detecting technology is utilized.

The ultrasonic flaw detecting technology relates to propagating ultrasonic waves onto the surface of a molded material through medium such as water, converting the sonic wave reflected from the front surface of the molded material, the flaw existing within the material, and the back surface of the material into electric signals, and thereby detecting the inner conditions of the molded material.

According to another method (the through transmission method), the inner flaw may be detected by propagating ultrasonic waves from one side of the molded material placed under water, and receiving the transmitted sonic waves.

FIG. 9 shows the principle of an ultrasonic flaw detector utilizing the through transmission method.

Water W is filled inside a tank 10, and a molded material $P_1$, which is the object of inspection, is positioned inside the tank.

Ultrasonic wave $V_1$ is propagated toward the molded material $P_1$ from a transmission search unit 20. A reception search unit 30 positioned to oppose to the unit 20 receives the transmitted sonic wave $V_2$, and detects flaw.

According to such device, the transmission search unit 20 and the reception search unit 30 must be operated in synchronism. Moreover, the transmitted ultrasonic wave $V_1$ must be converged to concentrate the energy, and therefore, it is difficult to detect the flaw formed to a corner portion $A_1$ and the like of the molded material $P_1$.

Therefore, a flaw detector utilizing a reflection method is provided.

Water $W_1$ is filled inside a tank 10, and a molded material $P_1$ is placed inside the tank 10. On one side wall of the tank 10 is positioned a plurality of search units 40, which are for transmitting and receiving ultrasonic waves.

Similarly, a plurality of search units 50 are positioned to the bottom of the tank 10, which are for transmitting and receiving ultrasonic waves.

FIG. 11 is an explanatory view showing the result of inspection performed according to the above flaw detector.

The ultrasonic wave $V_1$ transmitted from the search unit 40 is reflected by the front surface $S_1$ and the back surface $b_1$ of the molded material $P_1$, and a waveform as shown in FIG. 11 is drawn on an oscilloscope $O_1$.

In advance, a normal (good) back surface reflection level $L_1$ is set within the range of a gate $G_1$ as the back surface range width, using a sample.

FIG. 11 (A) shows the reflected wave of the solid (good) portion of the molded material $P_1$. The reflected wave $EB_1$ reflected by the back surface $B_1$ exists above the set level $L_1$ within the gate $G_1$, and therefore, the inspected portion is determined to be acceptable.

FIG. 11 (B) shows the state where a void $H_1$ so-called porosity is formed within the molded material $P_1$. When such a void $H_1$ exists, the reflected wave $EB_1$ is damped, and the level will not reach the set level $L_1$. As a result, the inspected portion is determined to be unacceptable.

FIG. 11 (C) shows the state where an exfoliated portion $F_1$ so-called a delamination exists near the back surface $B_1$ of the molded material $P_1$. If the molded material $P_1$ is manufactured by press forming plural sheets of laminated FRP films, delamination portion $F_1$ is likely to appear within the material.

When such defect exists, however, the reflected wave $EF_1$ from the delamination portion $F_1$ may exceed the set level $L_1$ within the gate portion $G_1$ set to the position corresponding to the back surface $B_1$, and the inspected portion may be determined to be acceptable.

Especially when the thickness of the molded material is small, such problem occurs.

SUMMARY OF THE INVENTION

Therefore, the present invention aims at solving the above problems of the prior art by providing a device capable of detecting the flaw existing within the object molded material correctly, even if the molded material is formed of composite material.

The automatic ultrasonic flaw detector according to the present invention comprises, as basic means, a flaw detection chamber filled with water and having an opening portion through which a molded material being the object of inspection travels; an ultrasonic search unit positioned within the chamber to oppose to one surface of an object portion of inspection of the molded material; an ultrasonic reflector plate positioned to oppose to said ultrasonic search unit and to have a predetermined distance from the other surface of said object portion of inspection; and an inspecting means for comparing the reflected signal of ultrasonic waves with the signal from a solid portion.

The detector further comprises rollers for gripping and sending the molded material into the flaw detection chamber, and bellows equipped to the opening portion of the flaw detection chamber through which the molded material travels, so that water within the chamber is prevented from leaking.

The reflector plates are formed as a unit removably placed within the flaw detection chamber, and the unit of reflector plates is divided into two parts with its boundary set along the opening portion of the flaw detection chamber.

DETAILED DESCRIPTION OF PREFERRED EMBODIMENTS

Figure 1:
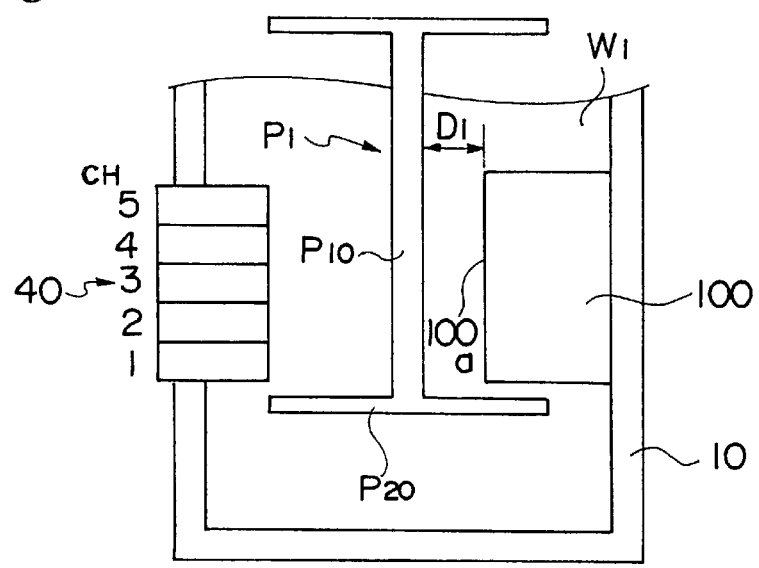
FIG. 1 is a front view showing the main area of the ultrasonic flaw detector according to the present invention.
Figure 2:
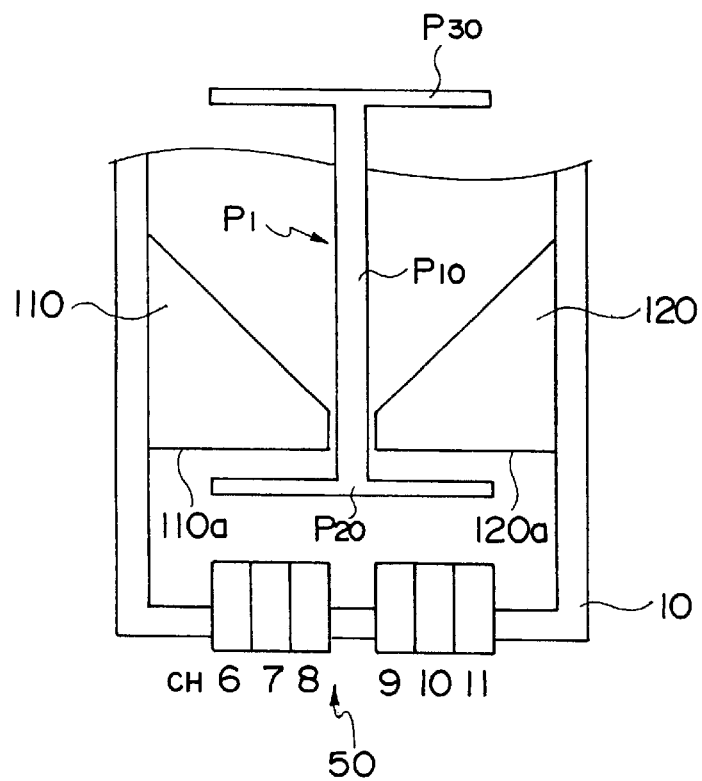
FIG. 2 is a front view showing the main area of the ultrasonic flaw detector according to the present invention.
Figure 3:
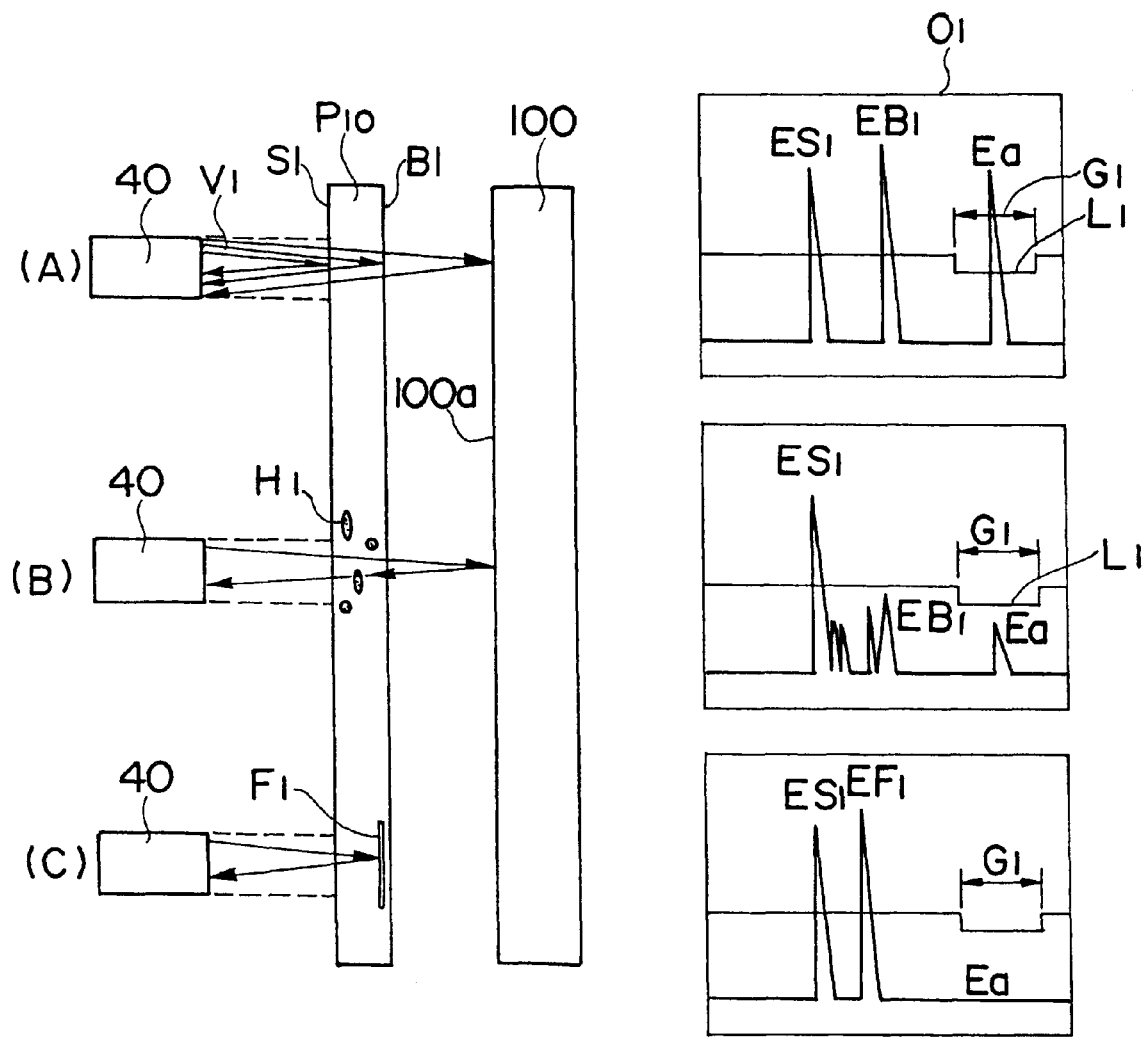
FIG. 3 is an explanatory view showing the action of the ultrasonic flaw detector according to the present invention.

FIGS. 1 and 2 are front views showing the main area of the ultrasonic flaw detector according to the present invention. FIG. 3 is an explanatory view showing its action.

According to FIG. 1, five ultrasonic search units 40 are arranged vertically on one side wall of a tank 10. The diameter of each ultrasonic search unit 40 is approximately 10 mm. A plural number of ultrasonic search units 40 are equipped to the tank according to the size of a molded material $P_1$, which is the object of inspection.

The molded material $P_1$ travels along the longitudinal direction by a guide device explained later. On the other side wall of the tank 10 is equipped a reflector plate 100.

The reflector plate 100 includes a reflection surface 100a. The reflection surface 100a is positioned away by a distance $D_1$ from the back surface of an object portion $P_{10}$ being inspected, and reflects the ultrasonic waves from the five search units 40.

If the molded material $P_1$ being inspected has a T-shaped or H-shaped cross section, ultrasonic search units 50 are placed on the bottom of the tank 10, and two reflector plates 110 and 120 are mounted opposing to an object portion $P_{20}$ of inspection of the molded material $P_1$. The first reflector plate 110 is positioned so as to reflect the sonic waves from three search units corresponding to channels 6, 7 and 8. The second reflector plate 120 is positioned so as to reflect the sonic waves from three search units corresponding to channels 9, 10 and 11.

When inspection of the object portions $P_{10}$ and $p_{20}$ are finished, the molded material $P_1$ is placed up side down, and the remaining object portions $P_{10}$ and $P_{30}$ are then inspected.

In FIG. 3, the ultrasonic wave $V_1$ irradiated from the search unit 40 is reflected by the front and back surfaces of the object portion $P_{10}$ and the reflection surface 100a of the reflector plate 100, and a pulse waveform as shown in FIG. 3 is drawn on an oscilloscope $O_1$. A gate $G_1$ is set to the position of the reflection surface 100a.

When the object portion $P_{10}$ is good (solid), the pulse Ea of the reflected wave is greater than a set level $L_1$ as shown in (A), and the object portion is determined to be accepted.

As shown in (B), when porosity $H_1$ exists within the object portion, the reflected wave is damped, and the waveform Ea will not reach the set level. Therefore, the object portion is determined to be unacceptable.

Next, as shown in (C), when a delamination $F_1$ exists within the object portion, the ultrasonic wave is reflected by the delamination $F_1$, and the reflected wave from the reflector plate 100a defined by the gate $G_1$ disappears. Therefore, the object portion is determined to be unacceptable.

Since the reflector plate 100 is positioned away from the surface of the inspected portion, the position of the gate $G_1$, is also clearly distinguished from the inspected surface, which improves the inspection accuracy.

Figure 4:
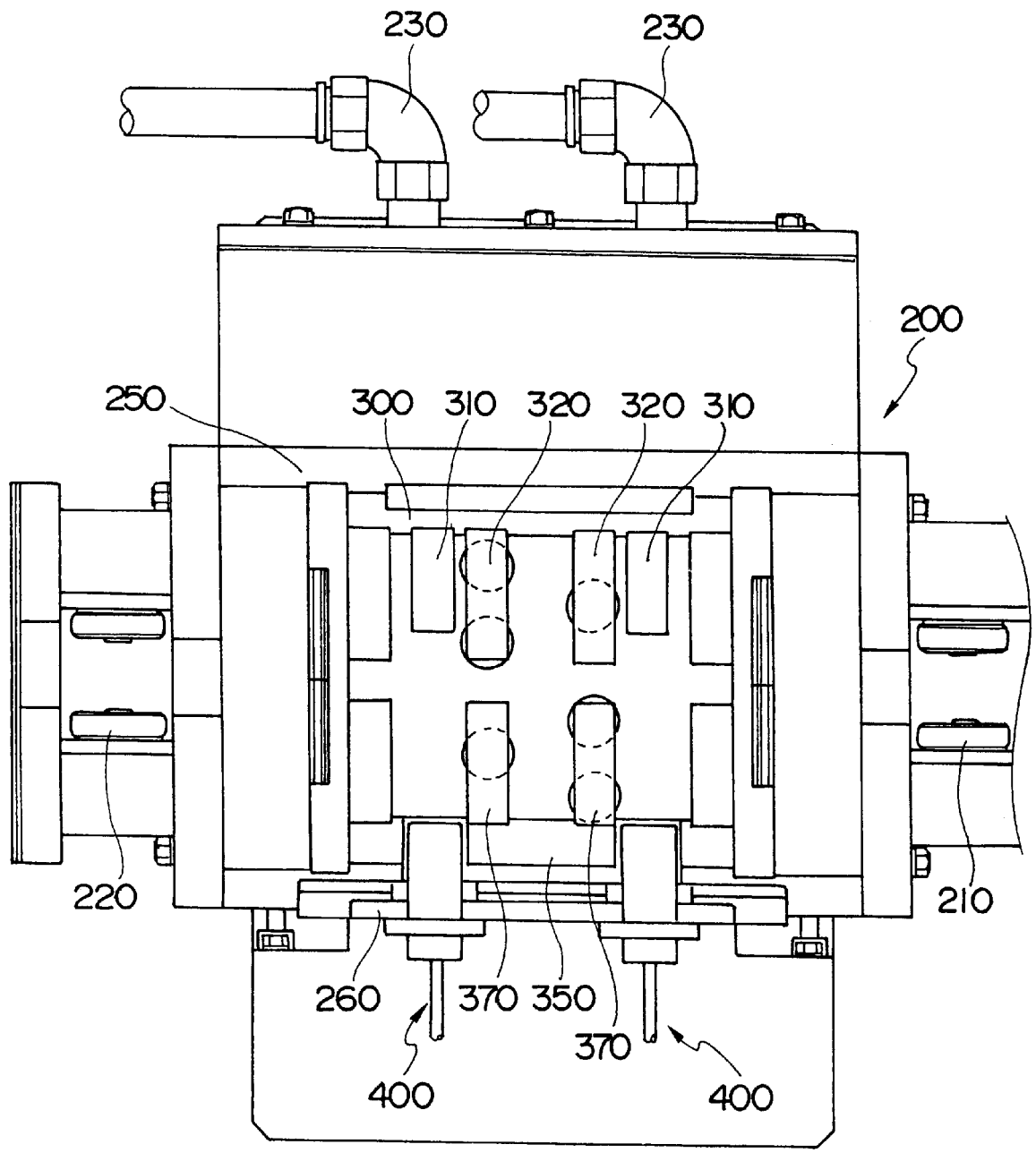
FIG. 4 is a plan view showing the main area of the ultrasonic flaw detector according to the present invention.
Figure 5:
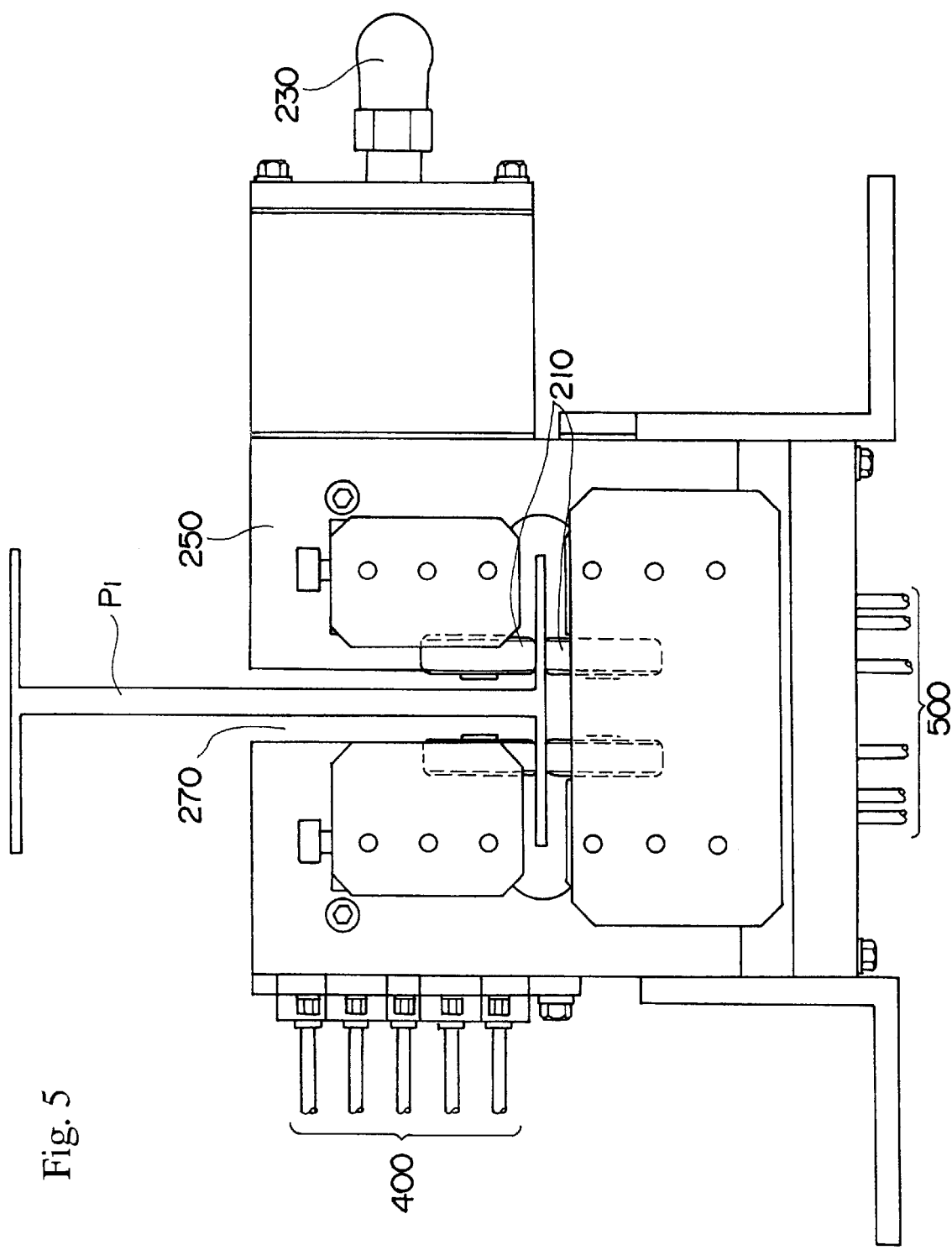
FIG. 5 is a side view showing the main portion of the ultrasonic flaw detector according to the present invention.

FIG. 4 is a plan view showing the main portion of the automatic ultrasonic flaw detector, and FIG. 5 is a side view thereof.

The ultrasonic flaw detector 200 includes a box-shaped ultrasonic flaw detection chamber 250, and water is supplied to the interior of the flaw detection chamber 250 through a pipeline 230.

Transmission rollers 210 and 220 are each mounted to the front and back areas of the flaw detection chamber 250, which grip the molded material $P_1$ and send it through the flaw detection chamber 250. A pair of reflector plate units 300 and 350 is removably mounted to the interior of the flaw detection chamber 250.

A search unit 400 for vertical direction search is mounted on one side wall 260 of the flaw detection chamber 250. The search unit 400 includes, for example, five search units arranged vertically with predetermined intervals.

A search unit 500 for transverse direction search is mounted on the bottom of the flaw detection chamber 250. The transverse direction search unit 500 includes, for example, six search units arranged transversely with predetermined intervals.

The first reflector plate unit 300 comprises a pair of reflector plates 310 opposing to the vertical search unit 400, and a pair of reflector plates 320 opposing to the transverse search unit 500.

The second reflector plate unit 350 comprises a pair of reflector plates 370 opposing to the transverse search unit 500.

Figure 6:
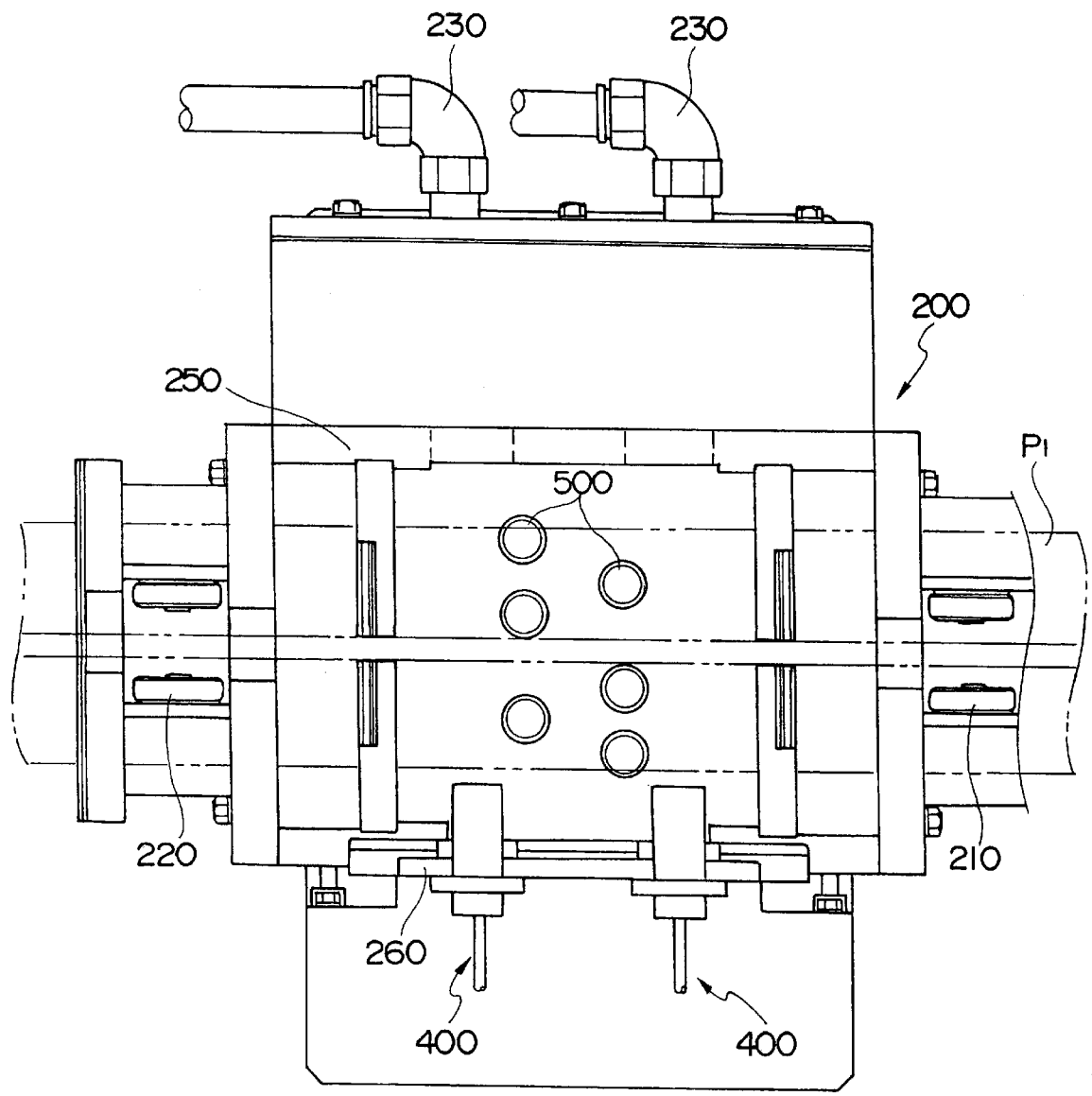
FIG. 6 is a plan view showing the ultrasonic flaw detector with the reflector plate units removed.

FIG. 6 is a plan view showing the ultrasonic flaw detector with the reflector plate unit removed.

The position of the vertical search unit 400 and the transverse search unit 500 inside the flaw detection chamber 250 is shown.

Figure 7:
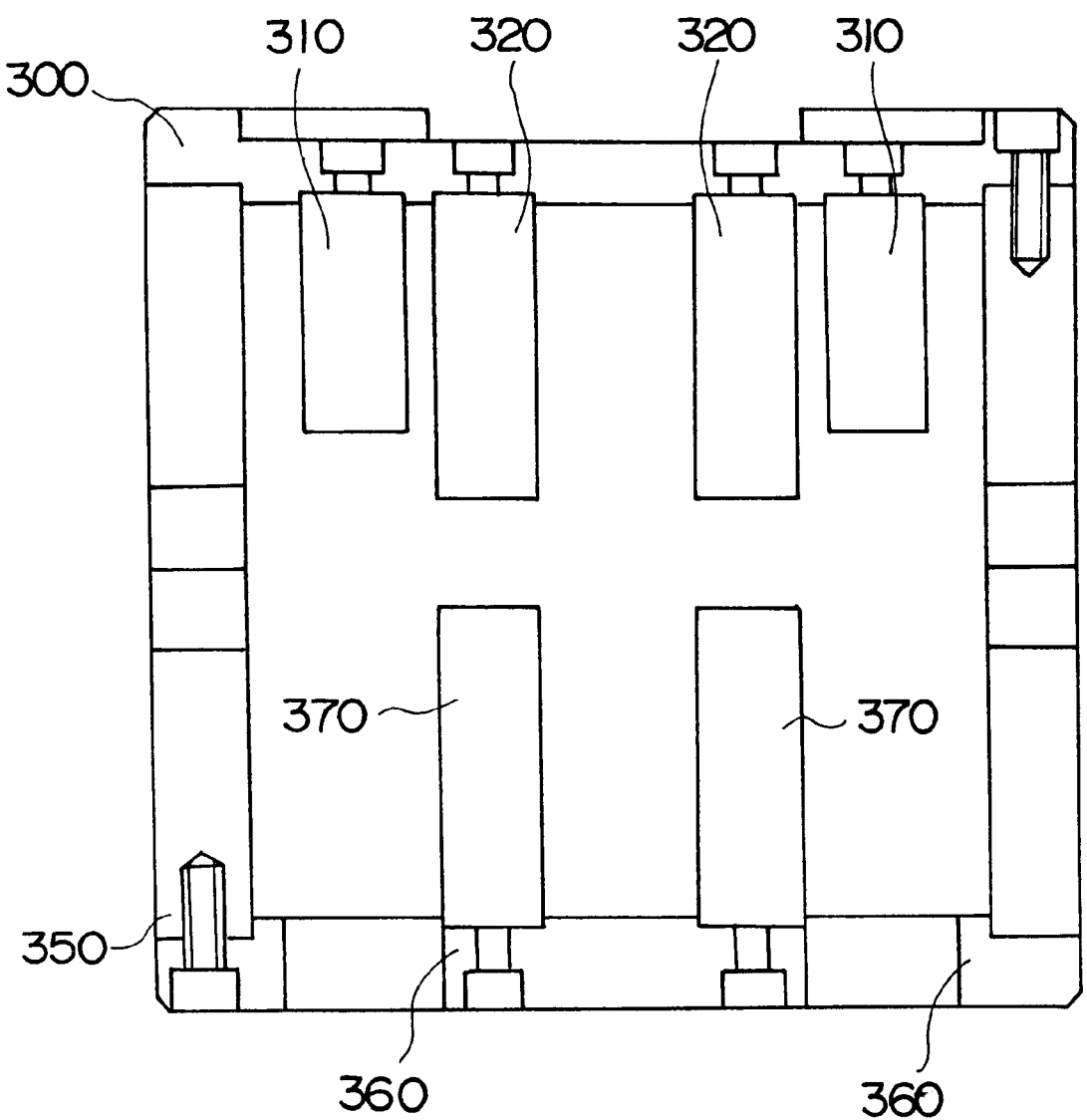
FIG. 7 is a plan view of the reflector plate units.
Figure 8:
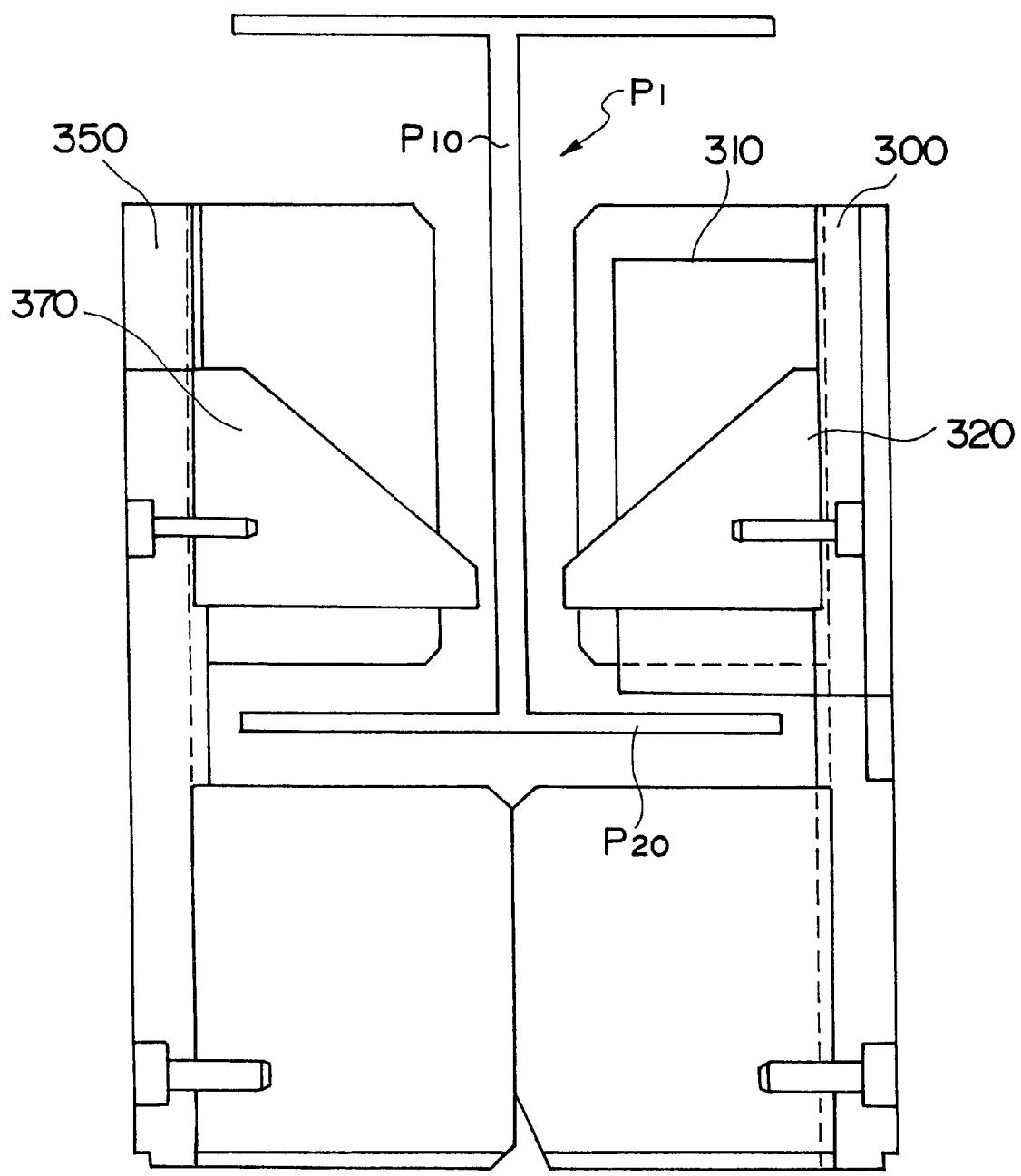
FIG. 8 is a side view of the reflector units.
Figure 9:
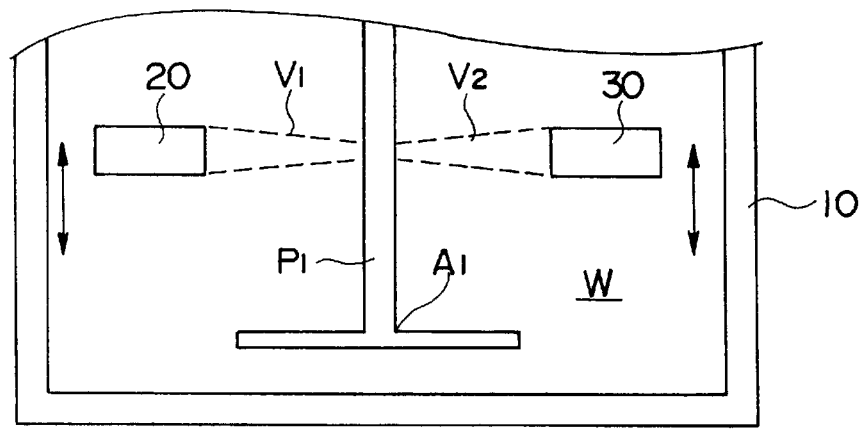
FIG. 9 is an explanatory view showing the ultrasonic flaw detector utilizing the through transmission method.
Figure 10:
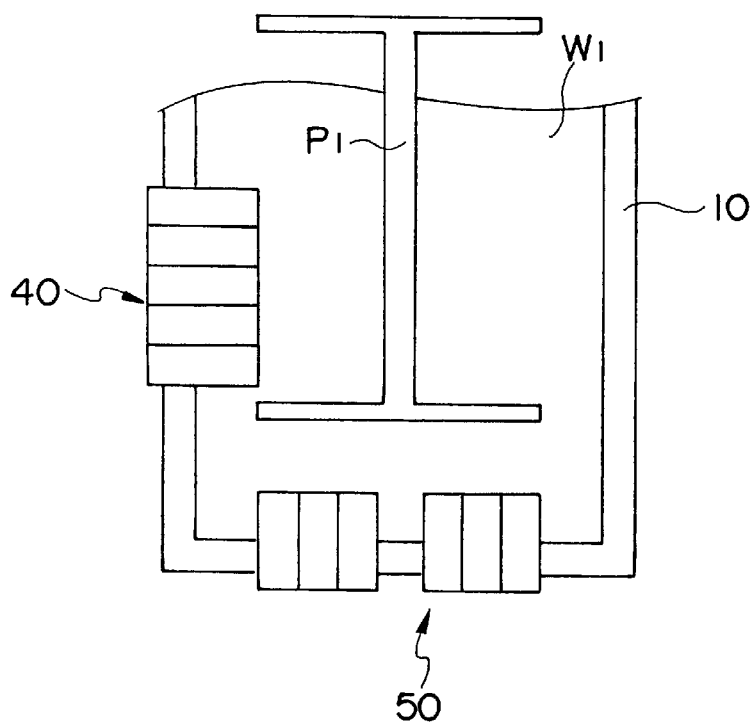
FIG. 10 is an explanatory view showing the ultrasonic flaw detector utilizing the reflection method.
Figure 11:
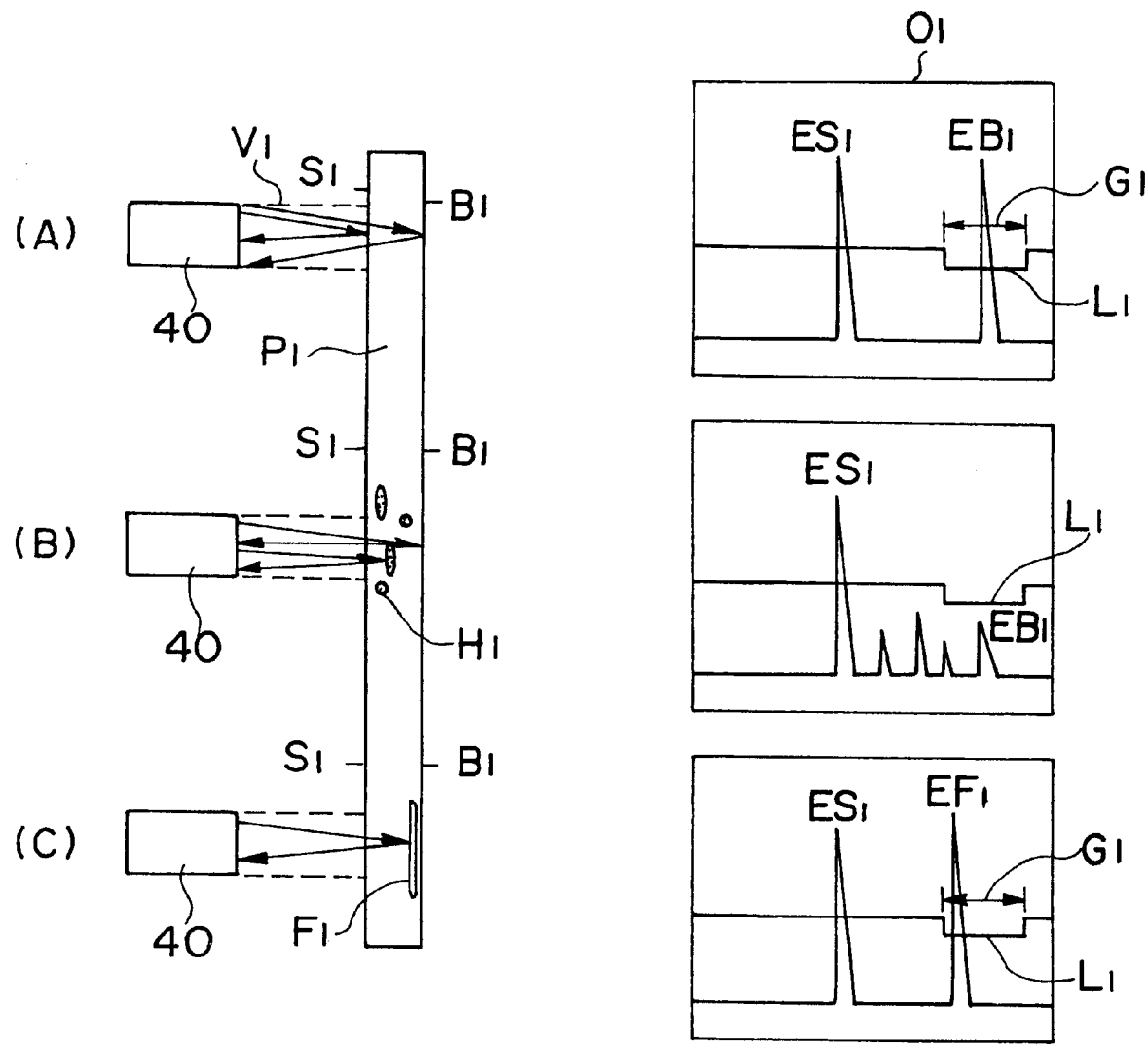
FIG. 11 is an explanatory view showing the action of the ultrasonic flaw detector utilizing the reflection method.

FIG. 7 is a plan view of the reflector plate unit, and FIG. 8 is a side view thereof.

The reflector plate units 300 and 350 can be inserted from the upper area of the flaw detection chamber 250. The plate units 300 and 350 can also be removed for cleaning the reflection surfaces and the like.

Further, water is filled within the flaw detection chamber 250, and as shown in FIG. 5, an opening portion 270 is equipped to the chamber enabling the molded material to pass through into the chamber. Bellows are equipped to the opening portion 270, so as to minimize the leakage of water, and at the same time, air is injected to the bellows from the outside, thereby preventing water from leaking.

As explained above, the ultrasonic flaw detector according to the present invention includes reflector plates equipped within a flaw detection chamber for reflecting the ultrasonic waves. The molded material, which is the object of inspection, is moved along a longitudinal direction in the chamber, in order to perform the flaw detection continuously. Therefore, the inspection efficiency is very high, and the flaw detection accuracy is improved.

I claim:

1. An automatic ultrasonic flaw detector comprising:

a flaw detection chamber filled with water and having an opening portion through which a molded material to be inspected enters;

more than one ultrasonic search unit positioned within said chamber opposite a first surface of an object portion of said molded material to be inspected;

more than one ultrasonic reflector plate positioned opposite said ultrasonic search unit and being spaced apart a predetermined distance from a second surface of said object portion of said molded material to be inspected; and an inspecting means for comparing a reflected signal of ultrasonic waves directed toward said object portion of said molded material to be inspected with a signal from a solid good portion.

2. The automatic ultrasonic flaw detector according to claim 1, further comprising rollers for gripping and sending said molded material into said flaw detection chamber.

3. The automatic ultrasonic flaw detector according to claim 1, further comprising bellows equipped to said opening portion of said flaw detection chamber through which said molded material travels, so that water within said chamber is prevented from leaking.

4. The automatic ultrasonic flaw detector according to claim 1, wherein a plural number of said reflector plates are formed as a unit, which is removably placed within said flaw detection chamber.

5. The automatic ultrasonic flaw detector according to claim 4, wherein said unit of reflector plates is divided into two parts with its boundary set along said opening portion of said flaw detection chamber.

* * * * *